United States Patent
Levell

(12) 
(10) Patent No.: US 6,620,141 B2
(45) Date of Patent: Sep. 16, 2003

(54) VALVE ASSEMBLY APPARATUS

(76) Inventor: David B. Levell, 5925 Pebble Beach Blvd., Las Vegas, NV (US) 89108

( * ) Notice: Subject to any disclaimer, the term of this patent is extended or adjusted under 35 U.S.C. 154(b) by 0 days.

(21) Appl. No.: 09/891,810

(22) Filed: Jun. 26, 2001

(65) Prior Publication Data

US 2002/0002356 A1 Jan. 3, 2002

Related U.S. Application Data

(60) Provisional application No. 60/214,716, filed on Jun. 29, 2000.

(51) Int. Cl.[7] ................................................ A61M 1/00
(52) U.S. Cl. ........................................ 604/319; 251/149
(58) Field of Search ......................... 604/319, 322–324, 604/335, 30, 31, 167.03, 236, 247, 278, 288.03, 350, 317, 318, 320, 321, 325, 326; 251/12, 149, 148, 152, 143

(56) References Cited

U.S. PATENT DOCUMENTS

| | | | |
|---|---|---|---|
| 4,160,383 A | * | 7/1979 | Rauschenberger .......... 137/588 |
| 4,334,537 A | | 6/1982 | Peterson |
| 4,559,049 A | | 12/1985 | Haan |
| 4,725,268 A | | 2/1988 | Ostensen |
| 4,753,642 A | | 6/1988 | Nilsson |
| 4,795,449 A | * | 1/1989 | Schneider et al. .......... 604/129 |
| 5,356,386 A | | 10/1994 | Goldberg et al. |
| 5,460,603 A | * | 10/1995 | DeSantis ..................... 604/122 |
| 5,741,237 A | * | 4/1998 | Walker ......................... 134/50 |
| 5,931,822 A | * | 8/1999 | Bemis et al. ................ 604/317 |
| 5,954,704 A | * | 9/1999 | Sherman ................ 128/200.24 |

\* cited by examiner

Primary Examiner—Weilun Lo
Assistant Examiner—C. Lynne Anderson

(57) ABSTRACT

A valve assembly apparatus includes a main body portion which includes a top main body portion and a bottom main body portion. The bottom main body portion includes a container connector portion. A one-way vent valve is in air way communication with the bottom main body portion. A one-way liquid flow valve is supported by the main body portion. A tubing adaptor is connected to the top main body portion. The valve assembly apparatus can be used to direct urine from a urinary drainage tube into a urine reception container. The one-way liquid flow valve prevents urine from flowing backward up into the urinary drainage tube, and the one-way vent valve prevents urine from leaking from the urine reception container if the container is tipped over.

4 Claims, 3 Drawing Sheets

VALVE ASSEMBLY APPARATUS

CROSS-REFERENCE TO RELATED APPLICATION

This application claims priority based upon my copending Provisional Application Ser. No. 60/214,716, filed Jun. 29, 2000.

BACKGROUND OF THE INVENTION

1. Field of the Invention

The present invention relates generally to valve assemblies and, more particularly, to a valve assembly especially adapted for use with a container used for receiving urine from a person.

2. Description of the Prior Art

When a patient needs one's urine received in a container, it is often that thin vinyl urinary drainage bed bags are employed to collect the urine. Often, some of such bags are defective and have leaks from even the start of their use. Others of such bags have weak seams or become over extended and burst, causing stains, odors, unsanitary conditions, and difficult (and potentially costly) clean-up problems. Generally, such thin vinyl urinary drainage bed bags are relatively weak. Their inherent weakness is a major cause of their leaking and bursting. In this respect, it would be desirable if a urine collecting system were provided for a patient that is relatively strong and has a container that is not readily susceptible to leaking or bursting.

With a container that collects urine, there is always a risk that the container may tip or be knocked over. When such a container tips or is knocked over, urine that has already been collected may leak from the urine collection container. Moreover, even if a urine collection container itself would not leak if knocked over, there would be a risk that some other components of a urine collecting system would leak if the urine collection container were knocked over. Such other components would include tubes and valves that direct urine from the patient to the urine collection container. With particular attention to valves, it would be desirable if a urine collecting system were provided which has valves which will not permit urine to leak, even of a urine collection container were knocked over.

When urine leaves a patient's bladder, and passes through and exits the uro-genital system, such urine should not reflux and reverse its direction of flow. If such would occur, the patient would run the risk of uro-genital and bladder infections. To preclude urinary reflux from the urine collection container, it would be desirable if a one-way valve were provided that prevents urine backflow from the urine collection container to the patient.

In general, when an empty container receives a quantity of liquid, air in the container is displaced by the liquid. With a urine collecting system, it would be desirable if a vent valve were provided that permits air to escape from a container when the container receives urine.

Moreover, such a vent valve should be prevented from leaking out urine if the urine collection container is knocked over. In this respect, it would be desirable if a urine collecting system were provided which includes a vent valve which has features which prevent urine from leaking through the vent valve if a urine collection container is knocked over.

The thin vinyl urinary drainage bed bags mentioned above are specially designed for receiving urine. In this respect, they are medical items. In some localities, such bags are not readily available. Also, in some localities, such bags can be obtained only with a doctor's prescription. As such, they are relatively costly, and they may be inconvenient to acquire, especially when one is travelling. Moreover, such thin vinyl urinary drainage bed bags are for most practical purposes, single use items. As a result, continuous use of such drainage bed bags is relatively costly. However, since urine is a waste item, it would be desirable if a urine collection container could be used that is not regarded as a medical item and that is reusable many times. Such features would provide significant cost savings and greater convenience.

Aside from the devices discussed above, throughout the years, a number of additional innovations have been developed relating to urine collecting systems, and the following U. S. patents are representative of some of those innovations: U.S. Pat. Nos. 4,334,537, 4,559,049, 4,725,268, 4,753,642, and 5,356,386. More specifically, U.S. Pat. No. 4,334,537 discloses a liquid check valve connected to a urine collection container at one location and an air vent connected to the urine collection container at another location. For purposes of efficiency and economy, it would be desirable if a liquid check valve and an air vent valve were provided on a common structure which is connected to a urine collection container at one location.

U.S. Pat. No. 4,559,049 discloses a liquid check valve but does not disclose an air vent valve. For reasons mentioned above, the presence of an air vent valve is desirable.

U.S. Pat. No. 4,725,268 discloses an anti-reflux valve and an air vent for a urine collection container. The air vent is made from microporous hydrophobic material which impedes the outflow of urine from the urine collection container in the event of the container being knocked over. However, the microporous hydrophobic material allows air flow in a two way direction. Moreover, the microporous hydrophobic material is not pressure resistant. That is, the more pressure behind any urine, the greater the amount of urine that can seep through the microporous hydrophobic material. In contrast, however, it would be desirable if a vent valve responded to pressure build up in a different way. That is, the greater the pressure behind the urine, the greater shut-off action of the vent valve.

U.S. Pat. No. 4,753,642 discloses a container valve assembly which contains a buoyant body inside the valve body. For purposes of simplicity, it would be desirable if a urine collecting system were provided which does not include a buoyant body inside a valve body.

U.S. Pat. No. 5,356,386 discloses an apparatus for locating body cavities. The apparatus employs fluctuating pressure and a responsive sensor. Generally, a urine collecting system does not need either fluctuating pressure or a responsive sensor.

Thus, while the foregoing body of prior art indicates it to be well known to use urine collecting systems, the prior art described above does not teach or suggest a urine collecting system which has a valve assembly apparatus and which has the following combination of desirable features: (1) provides a urine collecting system for a patient that is relatively strong and has a container that is not readily susceptible to leaking or bursting; (2) has valves which will not permit urine to leak, even of a urine collection container is knocked over; (3) provides a one-way valve that prevents urine backflow from the urine collection container to the patient; (4) provides a vent valve that permits air to escape from a container when the container receives urine; (5) includes a vent valve which has features which prevent urine from leaking through the vent valve if a urine collection container is knocked over; (6) permits a urine collection container to be used that is not a medical item and that is reusable many times; (7) provides a liquid check valve and an air vent valve in a common structure which is connected to a urine collection container at one location; (8) provides a vent valve in which the greater the pressure behind the urine, the greater the shut-off action of the vent valve; and (9) does not include a buoyant body inside a valve body. The foregoing desired characteristics are provided by the unique valve assembly apparatus of the present invention as will be made apparent from the following description thereof. Other advantages of the present invention over the prior art also will be rendered evident.

SUMMARY OF THE INVENTION

To achieve the foregoing and other advantages, the present invention, briefly described, provides a valve assembly apparatus which includes a main body portion which includes a top main body portion and a bottom main body portion. The bottom main body portion includes a container connector portion. A one-way vent valve is in air way communication with the main body portion. A one-way liquid flow valve is supported by the main body portion. A tubing adaptor is connected to the top main body portion. The one-way vent valve is in air way communication with the bottom main body portion.

The tubing adaptor includes a bottom tubing adaptor end which is connected to the top main body portion and includes a top tubing adaptor end. The top main body portion includes internal threads, and the bottom tubing adaptor end includes external threads. The top main body portion includes an internal valve-reception ledge, and the one-way liquid flow valve includes a support flange which rests upon the internal valve-reception ledge.

The container connector portion includes internal threads for connection with external threads on the top neck of the urine reception container. The one-way liquid flow valve is a flap valve. The one-way vent valve is a ball valve. The ball valve includes ball valve member.

The valve assembly apparatus can be used to direct urine from a urinary drainage tube into a urine reception container. The one-way liquid flow valve prevents urine from flowing backward up into the urinary drainage tube, and the one-way vent valve prevents urine from leaking from the urine reception container if the container is tipped over.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining a preferred embodiment of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved valve assembly apparatus which has all of the advantages of the prior art and none of the disadvantages.

It is another object of the present invention to provide a new and improved valve assembly apparatus which may be easily and efficiently manufactured and marketed.

It is a further object of the present invention to provide a new and improved valve assembly apparatus which is of durable and reliable construction.

An even further object of the present invention is to provide a new and improved valve assembly apparatus which is susceptible of a low cost of manufacture with regard to both materials and labor, and which accordingly is then susceptible of low prices of sale to the consuming public, thereby making such valve assembly apparatus available to the buying public.

Still yet a further object of the present invention is to provide a new and improved valve assembly apparatus which provides a urine collecting system for a patient that is relatively strong and has a container that is not readily susceptible to leaking or bursting.

Still another object of the present invention is to provide a new and improved valve assembly apparatus that has valves which will not permit urine to leak, even of a urine collection container is knocked over.

Yet another object of the present invention is to provide a new and improved valve assembly apparatus which provides a one-way valve that prevents urine backflow from the urine collection container to the patient.

Even another object of the present invention is to provide a new and improved valve assembly apparatus that provides a vent valve that permits air to escape from a container when the container receives urine.

Still a further object of the present invention is to provide a new and improved valve assembly apparatus which includes a vent valve which has features which prevent urine from leaking through the vent valve if a urine collection container is knocked over.

Yet another object of the present invention is to provide a new and improved valve assembly apparatus that permits a urine collection container to be used that is not a medical item and that is reusable many times.

Still another object of the present invention is to provide a new and improved valve assembly apparatus which provides a liquid check valve and an air vent valve in a common structure which is connected to a urine collection container at one location.

Yet another object of the present invention is to provide a new and improved valve assembly apparatus that provides a vent valve in which the greater the pressure behind the urine, the greater the shut-off action of the vent valve.

Still a further object of the present invention is to provide a new and improved valve assembly apparatus that does not include a buoyant body inside a valve body.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein.

DESCRIPTION OF THE PREFERRED EMBODIMENT

With reference to the drawings, a new and improved valve assembly apparatus embodying the principles and concepts of the present invention will be described.

Figure 1:
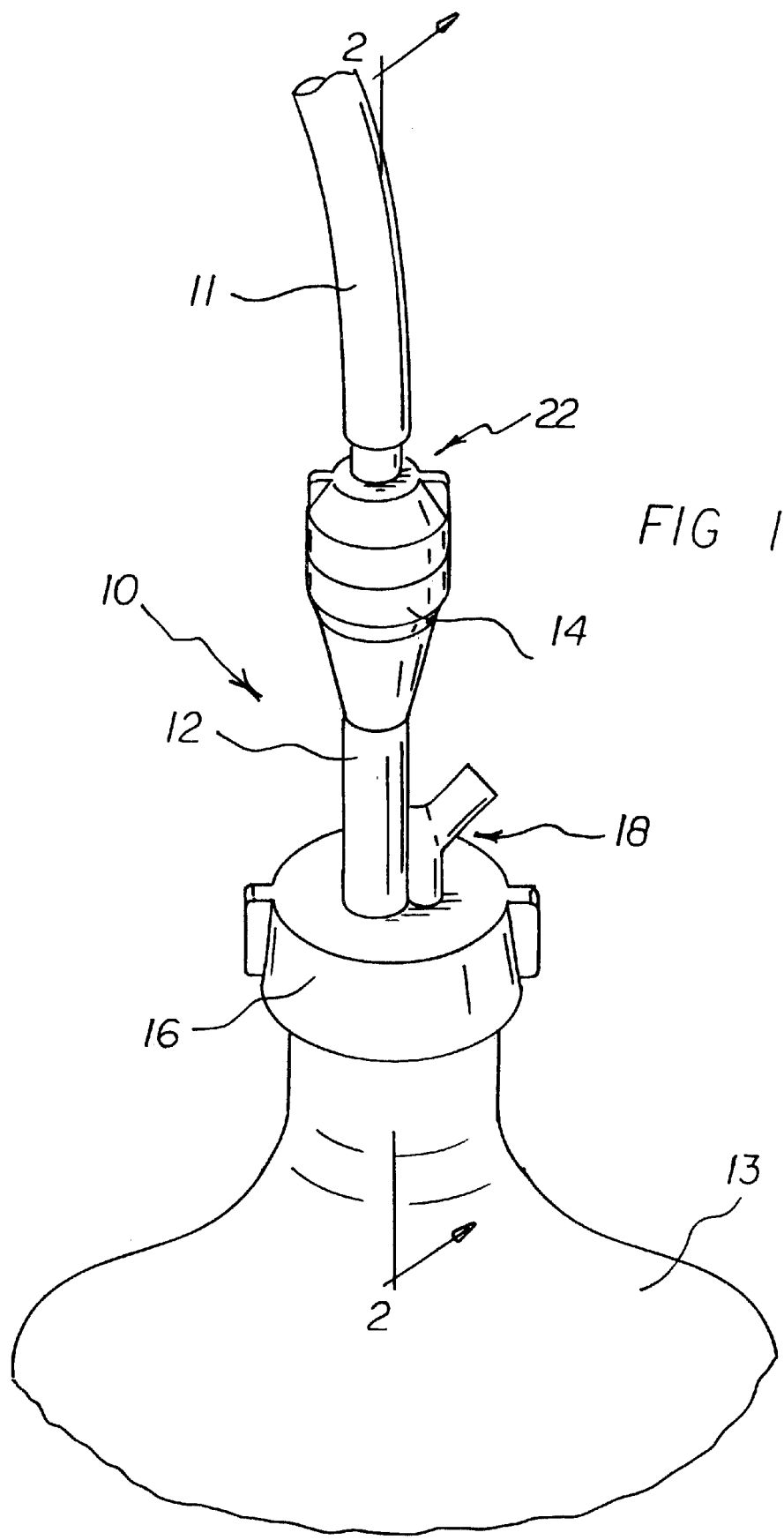
FIG. 1 is a top perspective view showing a preferred embodiment of the valve assembly apparatus of the invention connected between a urinary drainage tube and a urine reception container.
Figure 2:
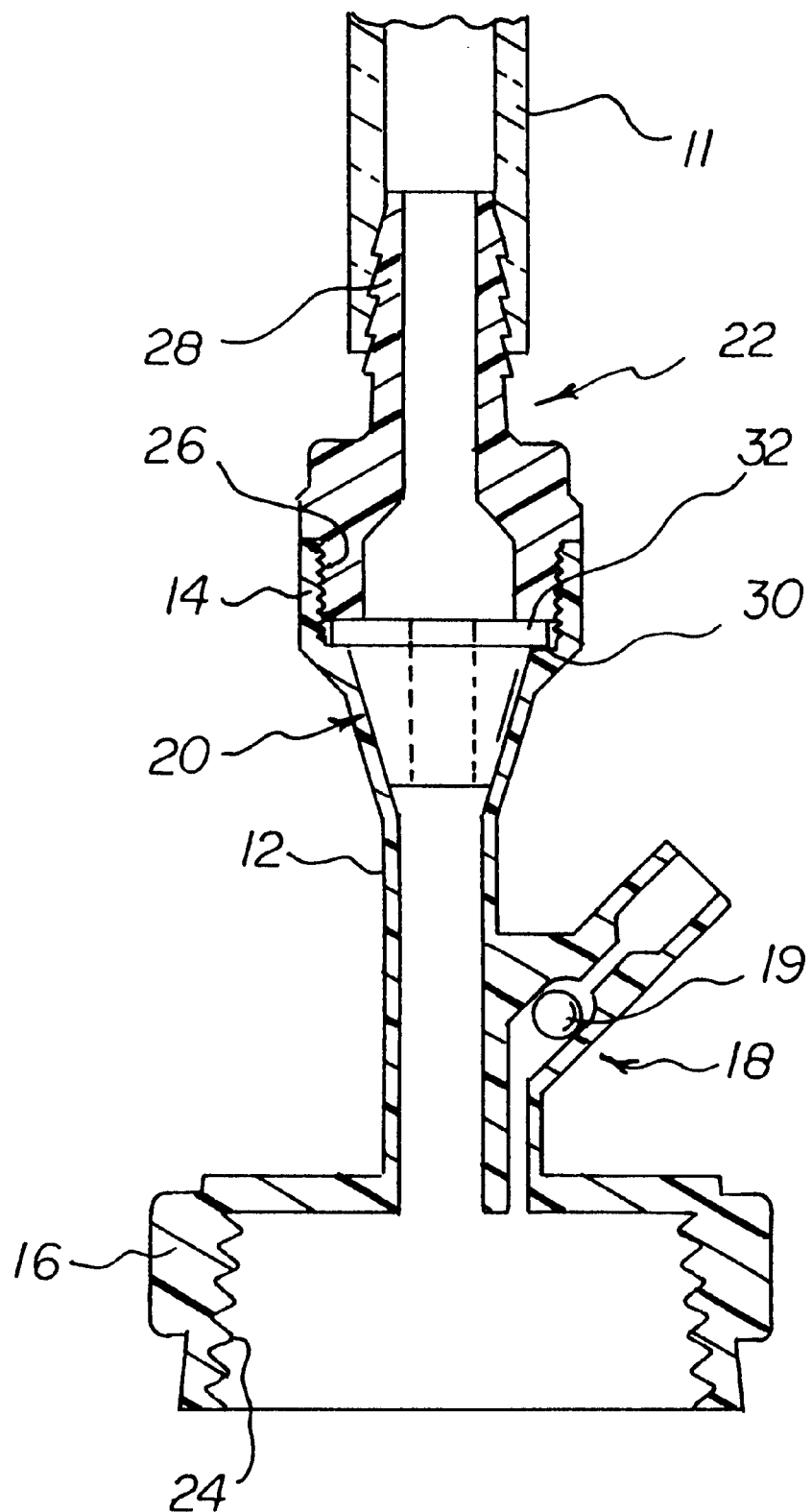
FIG. 2 is a cross-sectional view of the embodiment of the valve assembly apparatus of FIG. 1 taken along line 2—2 thereof.
Figure 3:
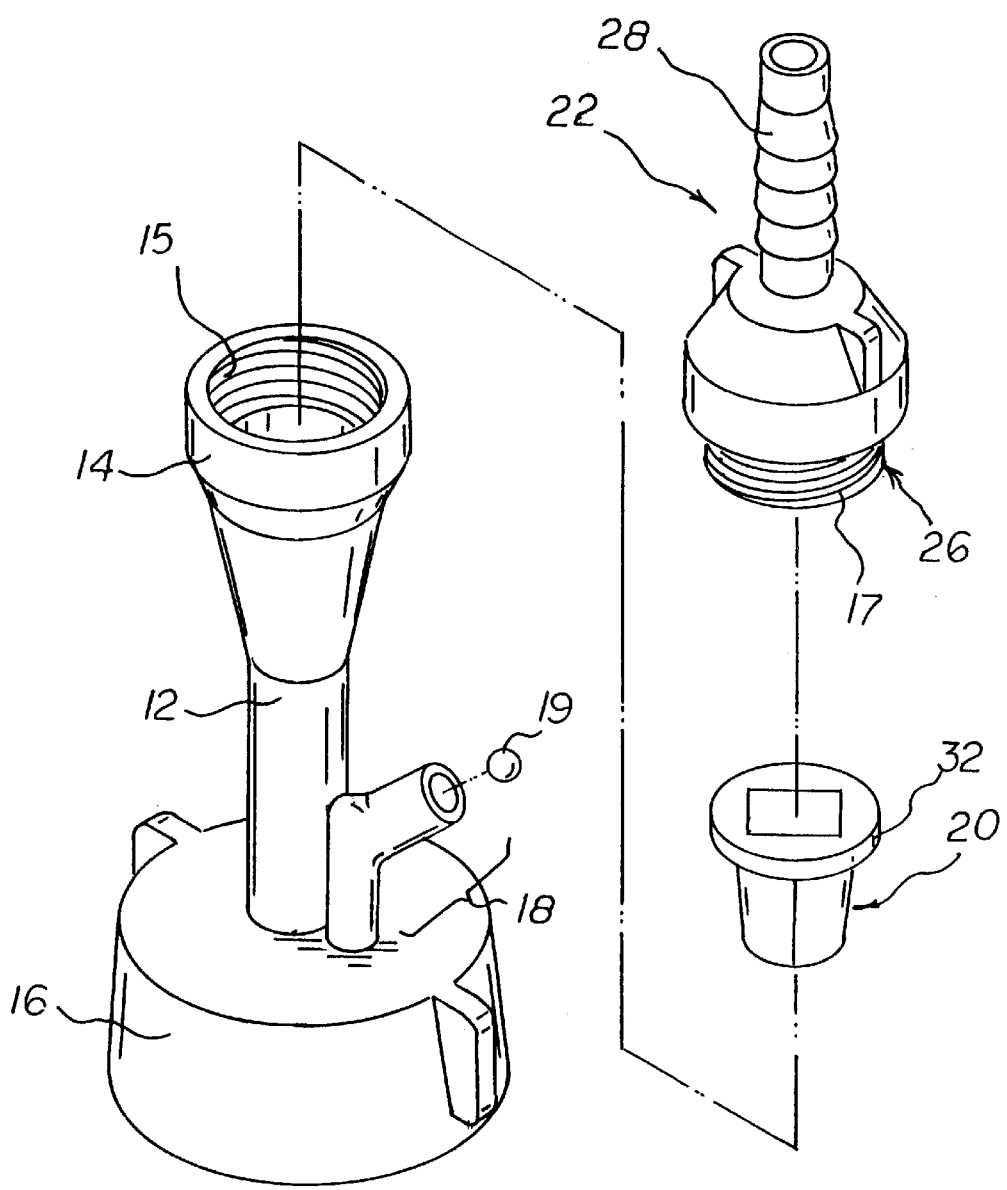
FIG. 3 is an exploded perspective view of the embodiment of the invention shown in FIGS. 1 and 2.

Turning to FIGS. 1–3, there is shown an exemplary embodiment of the valve assembly apparatus of the invention generally designated by reference numeral 10. In its preferred form, valve assembly apparatus 10 includes a main body portion 12 which includes a top main body portion 14 and a bottom main body portion 16. The bottom main body portion 16 includes a container connector portion 24. A one-way vent valve 18 is in air way communication with the main body portion 12. A one-way liquid flow valve 20 is supported by the main body portion 12. A tubing adaptor 22 is connected to the top main body portion 14. The one-way vent valve 18 is in air way communication with the bottom main body portion 16.

The tubing adaptor 22 includes a bottom tubing adaptor end 26 which is connected to the top main body portion 14 and includes a top tubing adaptor end 28. The top main body portion 14 includes internal threads 15, and the bottom tubing adaptor end 26 includes external threads 17. The top main body portion 14 includes an internal valve-reception ledge 30, and the one-way liquid flow valve 20 includes a support flange 32 which rests upon the internal valve-reception ledge 30.

The container connector portion 24 includes internal threads for connection with external threads on the top neck of the urine reception container 13. The one-way liquid flow valve 20 is a flap valve. The one-way vent valve 18 is a ball valve. The ball valve includes ball valve member 19.

Before using the valve assembly apparatus 10 of the invention, the apparatus is assembled. To do so, the one-way liquid flow valve 20 is placed inside the main body portion 12 so that the support flange 32 rests upon the internal valve-reception ledge 30 of the main body portion 12. Then, the external threads 17 of the tubing adaptor 22 are screwed into the internal threads 15 of the top main body portion 14. Then, the bottom of the tubing adaptor 22 presses upon the top of the support flange 32, thereby securing the one-way liquid flow valve 20 inside the main body portion 12. When the valve assembly apparatus 10 is fully assembled, the ball valve member 19 is located inside the one-way vent valve 18.

The environment in which the fully assembled valve assembly apparatus 10 of the invention is employed is illustrated in FIG. 1. One end of a urinary drainage tube 11 is connected to a patient (not shown) in a conventional way. The other end of the urinary drainage tube 11 is fitted onto the top tubing adaptor end 28 of the tubing adaptor 22. The threaded top of a urine reception container 13 is screwed into the container connector portion 24 of the bottom main body portion 16.

As urine from the patient flows down through the urinary drainage tube 11, the urine passes through the tubing adaptor 22, through the one-way liquid flow valve 20, through the main body portion 12, through the bottom main body portion 16, and into the urine reception container 13. The ball valve member 19 of the one-way vent valve 18 is normally in an open position so that air that is displaced from the urine reception container 13 by the urine can vent out from the urine reception container 13 through the one-way vent valve 18.

If the urine reception container 13 tips over, the one-way liquid flow valve 20 prevents liquid from flowing back up the urinary drainage tube 11, and the ball valve member 19 in the one-way vent valve 18 will be pushed by the urine in the tipped over urine reception container 13 to prevent urine from flowing out from the one-way vent valve 18.

When the urine reception container 13 is full, the urinary drainage tube can be pinched shut, and the urine reception container 13 can be unscrewed from the container connector portion 24 of the bottom main body portion 16. Then, an empty urine reception container 13 can replace the full one.

When the valve assembly apparatus 10 is to be cleaned, it can be disassembled, and the individual components can be cleaned. Then, the cleaned components can be reassembled and reused. The urine reception container 13 can be a durable, reusable, empty bleach container or the like. Such a durable, reusable container has a number of advantages over flimsy, disposable plastic bags which all-to-often rupture, causing an unsanitary and hard-to-clean-up mess. The reusable urine reception container 13 can be carried to locations where conventional, flaccid, plastic, urine-receiver bags are hard to locate and purchase.

The components of the valve assembly apparatus of the invention can be made from inexpensive and durable metal and plastic materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved urine collecting system which has a valve assembly apparatus that is low in cost, relatively simple in design and operation, and which may advantageously can be used with a urine collecting system for a patient that is relatively strong and has a container that is not readily susceptible to leaking or bursting. With the invention, a valve assembly apparatus is provided which has valves which will not permit urine to leak, even of a urine collection container is knocked over. With the invention, a valve assembly apparatus provides a one-way valve that prevents urine backflow from the urine collection container to the patient. With the invention, a valve assembly apparatus provides a vent valve that permits air to escape from a container when the container receives urine.

With the invention, a valve assembly apparatus is provided which includes a vent valve which has features which prevent urine from leaking through the vent valve if a urine collection container is knocked over. With the invention, a valve assembly apparatus is provided which permits a urine collection container to be used that is not a medical item and that is reusable many times. With the invention, a valve assembly apparatus provides a liquid check valve and an air vent valve in a common structure which is connected to a urine collection container at one location. With the invention, a valve assembly apparatus provides a vent valve in which the greater the pressure behind the urine, the greater the shut-off action of the vent valve. With the invention, a valve assembly apparatus is provided which does not include a buoyant body inside a valve body.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

Hence, the proper scope of the present invention should be determined only by the broadest interpretation of the appended claims so as to encompass all such modifications as well as all relationships equivalent to those illustrated in the drawings and described in the specification.

Finally, it will be appreciated that the purpose of the annexed Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed as being new and desired to be protected by Letters Patent of the United States is as follows:

1. A valve assembly apparatus for use with a urine reception container having a top neck portion and external threads on said top neck portion, said apparatus comprising:
   a main body portion which includes a top main body portion and a bottom main body portion, wherein said bottom main body portion includes a container connector portion,
   a one-way vent valve in air way communication with said main body portion,
   a removable one-way liquid flow valve supported by said top main body portion, and
   a tubing adaptor connected to said top main body portion,
   wherein said tubing adaptor includes a bottom tubing adaptor end connected to said top main body portion, and a top tubing adaptor end,
   wherein said top main body portion includes internal threads and said bottom tubing adaptor end includes external threads,
   wherein said top main body portion includes an internal valve-reception ledge,
   said one-way liquid flow valve includes a support flange which rests upon said internal valve-reception ledge, said support ledge being located between said internal threads of said top main body portion and said main body portion,
   wherein said bottom tubing adaptor end engages said one-way liquid flow valve support flange when said bottom tubing adaptor end is threadedly mated with said top main body portion to maintain said one-way liquid flow valve in fluid communication between said bottom tubing adaptor end and said main body portion,
   wherein said container connector portion includes internal threads for connection with said external threads on said top neck of the urine reception container, and
   wherein said one-way vent valve is a ball valve.

2. The apparatus of claim 1 wherein said one-way liquid flow valve is a flap valve.

3. The apparatus of claim 1 wherein said ball valve includes a ball valve member.

4. A valve assembly apparatus for use with a urine reception container having a top neck portion and external threads on said top neck portion, said apparatus comprising:
   a main body portion which includes a top main body portion and a bottom main body portion, wherein said bottom main body portion includes a container connector portion,
   a one-way vent valve in air way communication with said main body portion,
   a removable one-way liquid flow valve supported by said top main body portion, and
   a tubing adaptor connected to said top main body portion,
   wherein said tubing adaptor includes a bottom tubing adaptor end connected to said top main body portion, and a top tubing adaptor end,
   wherein said top main body portion includes internal threads and said bottom tubing adaptor end includes external threads,
   wherein said top main body portion includes an internal valve-reception ledge,
   said one-way liquid flow valve includes a support flange which rests upon said internal valve-reception ledge, said support ledge being located between said internal threads of said top main body portion and said main body portion,
   wherein said bottom tubing adaptor end engages said one-way liquid flow valve support flange when said bottom tubing adaptor end is threadedly mated with said top main body portion to maintain said one-way liquid flow valve in fluid communication between said bottom tubing adaptor end and said main body portion,
   wherein said container connector portion includes internal threads for connection with said external threads on said top neck of the urine reception container, and
   wherein said removable one-way liquid flow valve further includes a conical body portion depending from said support flange and said top main body portion further includes a conical portion depending from said valve-reception ledge for forming a seat for said conical portion of said valve when said bottom tubing adaptor end is threadedly mated with said top main body portion as aforesaid said conical portion being located between said main body portion and said valve-reception ledge.

* * * * *